United States Patent [19]
Adler-Moore et al.

[11] Patent Number: 5,670,166
[45] Date of Patent: *Sep. 23, 1997

[54] PHARMACEUTICAL FORMULATION AND PROCESS

[75] Inventors: Jill P. Adler-Moore, Altadena; William A. Ernst, San Dimas, both of Calif.

[73] Assignee: NeXstar Pharmaceuticals, Boulder, Colo.

[*] Notice: The term of this patent shall not extend beyond the expiration date of Pat. Nos. 5,656,287 and 5,660,856.

[21] Appl. No.: 468,956

[22] Filed: Jun. 6, 1995

Related U.S. Application Data

[63] Continuation of Ser. No. 85,673, Jun. 30, 1993, which is a continuation of Ser. No. 687,812, Apr. 19, 1991, abandoned.

[51] Int. Cl.$^6$ ............................................. A61K 9/127
[52] U.S. Cl. ............................................. 424/450
[58] Field of Search ................................. 424/450

[56] References Cited

U.S. PATENT DOCUMENTS

| | | | |
|---|---|---|---|
| 4,663,167 | 5/1987 | Berestein | 264/416 |
| 4,797,285 | 1/1989 | Barenholz et al. | 424/450 |
| 4,952,405 | 8/1990 | Young | 424/423 |
| 4,963,362 | 10/1990 | Rahman | 424/450 |
| 5,000,887 | 3/1991 | Tenzel et al. | 424/450 |
| 5,023,087 | 6/1991 | Yau-Young | 424/450 |

FOREIGN PATENT DOCUMENTS

| | | |
|---|---|---|
| 90/00389 | 1/1990 | WIPO. |
| 91/04019 | 4/1991 | WIPO. |

OTHER PUBLICATIONS

Dreamer: Liposome Prep. Chap I: 1983 p. 27.
L. Stuhne–Sekalec et al. "Liposomes as Carriers of Cyclosporin A", J. Microencapsulation 8, No. 4, 441–446, Oct. 17, 1991, U.S.
L. Stuhne–Sekalec et al. "Liposomes as Cyclosporin A Carriers: the Influence of ordering Hydrocarbon Chains of Phosphatidylglycerol Liposomes on the Association with and Topogra of Cyclosporin A", J. Microencapsulation 8, No. 3, 283–285, Aug. 23, 1991, UK.
Szoka, Ann. Rev. Biophys. Bioeng. 1980, 9, p. 447.
Stuhne–Sekalec, Co–encapsulation of cyclosporin and insulin by liposomes, J. Biochem. Biophys. Methods 13 (1986) 23–27.
Stuhne–Sekalec, Encapsulation of cyclosporin by phosphatidylinositol–cholesterol liposomes, Transplantation 4, 659–660 (1986).
Stuhne–Sekalec, Liposomes as cyclosporin a carriers: positively charged lecithin–cholesterol ... phosphatidylinositol, J. Microencapsulation 6 (1969) 177–182.
Hsieh et al., Preliminary Report: The use of liposome–encapsulated cyclosporine in a rat model Transplantation Proceedings, vol. XVII, pp. 1397–1399, Feb. 1985.
Venkataram, Pharmacokineitcs of two alternative dosage forms for cyclosporin: liposomes an intralipid, J. Pharm. Sci. 79:216–219, Mar. 1990.
Gruber et al., Liposomal formulation eliminates acute toxicity and pump incompatibility of parenteral cyclosporin, Pharm. Res. 6(7): 601, 602, 1989.
Stuhne–Seklac et al., Liposomes as cyclosporin A carriers: ESR study of cyclosporin a interaction with 1,2–dimyristoyl–n–3–phosphatidylglycerol liposomes. J. Microencapsulation 8, No. 4, 455–457, Oct. 17, 1991, UK.

*Primary Examiner*—Gollamudi S. Kishore
*Attorney, Agent, or Firm*—NeXstar Pharmaceuticals, Inc.

[57] ABSTRACT

A process for preparing a liposomal cyclosporin therapeutic formulation, which comprises dissolving a combination of a neutral and negatively charged phospholipid and a cyclosporin in an organic solvent; drying the solution to form a solid phase, and hydrating the solid phase in an aqueous solution having a pH ranging from 7.5 to 9.5.

8 Claims, 3 Drawing Sheets

PHARMACEUTICAL FORMULATION AND PROCESS

This is a continuation of copending application Ser. No. 08/085,673 filed on Jun. 30, 1993, still pending which is a continuation of Ser. No. 07/687,812 filed Apr. 19, 1991 now abandoned.

FIELD OF THE INVENTION

This invention relates to the fields of biochemistry and medicine, and in particular to a novel liposomal formulation and process. More specifically, it relates to a liposomal formulation containing the immunosuppressive agent cyclosporine and to its process of manufacture. This invention also relates to a liposomal cyclosporine formulation having reduced toxicity.

BACKGROUND OF THE INVENTION

The cyclosporins were discovered in 1970 by researchers in attempts to identify new antimicrobial agents. Cyclosporine (also known as cyclosporin A), a potent immunosuppressive agent, was isolated from two strains of imperfect fungi, *Cylindrocapon lucidum* Booth and *Tolypodadium inflatum* Gams.

Cyclosporins are hydrophobic, neutral, cyclical peptides which have essentially similar chemical and physical characteristics. Cyclosporine is a representative example, and consists of eleven amino acids with a total molecular weight of 1201. Cyclosporine is soluble in methanol, chloroform and ether and essentially insoluble in water. It is supplied for therapeutic purposes as either an intravenous preparation dissolved in a proprietary castor oil and alcohol, or an oral formulation dissolved in Labrophil and olive oil.

Cyclosporine is primarily used for treating allograft patients and has been used in experimental trials for autoimmune diseases. The use of this drug has greatly increased the survival rate of transplant patients since its advent in 1978.

Although cyclosporine is a very useful immunosuppressive agent, it can also be highly toxic when used for prolonged periods of time and/or at high doses, both of which are necessary to ensure graft acceptance. The most severe side effect associated with cyclosporine therapy is drug-induced nephrotoxicity. Vascular interstitial toxicity is the most common form of cyclosporine nephrotoxicity and can manifest itself as three different morphological lesions, occurring either alone or in combination. Although not all of these morphological changes associated with cyclosporine nephrotoxicity are unique to cyclosporine toxicity, if they are observed in combination with one another and there is also a corresponding high level of serum cyclosporine, the damage is probably a result of cyclosporine toxicity. Some individuals may show some of these adverse reactions at therapeutic doses (5 to 10 mg/kg/day) which produce trough levels of 200–500 ng/ml in whole blood and 20–60 ng/ml in serum. Renal toxicities can be monitored serologically by following the increase in creatinine levels. The increase in creatinine level is probably a direct result of arteriole constriction and blockage which would result in lower glomerular filtration rate and thus an increase in serum creatinine.

There are other adverse side reactions associated with cyclosporine treatment. These occur with varying frequencies depending on the type of transplant. They include symptoms, such as cardiovascular hypertension and cramps, skin hirsutism, gum hyperplasia, diarrhea, nausea, vomiting, hepatotoxicity, hematopoietic alterations including leukopenia and lymphoran, respiratory distress and sinusitis.

Other side effects associated with the intravenous delivery of cyclosporine are due to the intravenous carrier vehicle, Cremophor-El (CreL). CreL is a polyoxyethylated castor oil that is one of the best ionic surfactants used to dissolve lipophilic drugs. The most common of the adverse reactions associated with CreL administration has been anaphylaxis which results from a rapid release of histamine and causes increasing hypertension. It is also believed that part of the nephrotoxicity associated with cyclosporine treatment may be enhanced by CreL deposition and crystal formation within the kidney tubules. Other Studies have also shown a decrease in both renal blood flow and creatinine clearance in animals treated with CreL. Riconic acid, a component of CreL, has been shown to cause vasoconstriction which could also be linked to hypertension and decreased glomerular blood flow.

Efforts have been made to eliminate the toxicity of cyclosporine by incorporating the drug into liposomes for purposes of administration, thus eliminating the toxic castor oil vehicle. Liposomes are microscopic delivery vesicles made, in part, from phospholipids which form closed, fluid filled spheres when mixed with water. Phospholipid molecules are polar, having a hydrophilic ionizable head, and a hydrophobic tail consisting of long fatty acid chains. Thus, when sufficient phospholipid molecules are present with water, the tails spontaneously associate to exclude water while the hydrophilic phosphate heads interact with water. The result is a bilayer membrane in which the fatty acid tails converge in the newly formed membrane's interior and the polar heads point in opposite directions toward an aqueous medium. The polar heads at one surface of the membrane point toward the aqueous interior of the liposome. At the opposite surface, the polar heads interact with the surrounding aqueous medium. As the liposomes form, water soluble molecules will be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely liquid center.

There are many types of liposome preparation techniques which may be employed and which produce various types of liposomes. These can be selected depending on the use, the chemical intended to be entrapped, and the type of lipids used to form the bilayer membrane.

Those parameters which must be considered in producing an optimal liposome preparation are similar to those of other controlled release mechanisms. They are as follows: (1) high percent of chemical entrapment; (2) increased chemical stability; (3) low chemical toxicity; (4) rapid method of production; and (5) reproducible size distribution.

The first method described to encapsulate chemicals in liposomes involved production of multilamellar vesicles (MLVs). The MLV process involves dissolving the lipid components in a suitable solvent, evaporation of the solvent to form a dry lipid film, and hydration of the lipid film with an aqueous medium. The multilamellar vesicles which form are structures having generally more than three concentric bilayers. Lipophilic drugs are incorporated into the MLVs by codissolution of the drugs in the solvent phase, while hydrophilic drugs are entrapped between the bilayers with the hydration buffer. By increasing the length of time of hydration and gentle shaking of the resuspending lipid film, one can achieve a higher proportion of the aqueous phase per mole of lipid, and thus enhance hydrophilic drug encapsulation. The increased entrapment of aqueous buffer can also be achieved by using charged lipids.

Liposomes can also be formed as unilamellar vesicles (UVs), which have diameters up to 2 μm, but generally less than 1 μm.

There are several techniques which are used to produce unilamellar liposomes. Large unilamellar vesicles (LUV's) an be formed using the reverse-phase evaporation method. This is done by removing the organic phase of a sonicated emulsion of phospholipid, buffer and excess organic solvent under pressure. This technique is especially useful for encapsulating large volumes of aqueous phase containing hydrophilic molecules, such as ferritin, 25S RNA or SV-40 DNA. Maximum encapsulation of the LUV aqueous phase (65%) can be obtained if the ionic strength of the aqueous buffer is low (0.01M NACl); encapsulation decreases to 20% as the ionic strength is increased to 0.5M NACl. The size of the LUVs varies with the lipid and cholesterol Content. Vesicles formed from cholesterol and phospholipid with a 1:1 mole ratio, form a heterogeneous size distribution of vesicles with a mean diameter, based upon entrapped volume, of 0.47 μm and a size range of 0.17–0.8 μm. Vesicles prepared from similar phospholipid mixtures lacking cholesterol have a mean diameter of 0.18 μm and a size range of 0.1–0.26 μm.

The solvent infusion evaporation method can produce both larger or smaller UVs, depending on variations in the technique. To form larger UVs, phospholipids are dissolved in diethylether and injected into a buffer maintained at 55°–65° C. containing the material to be entrapped or injected. The mixture is kept under vacuum at 30° C. When the solvent has evaporated, vesicles are formed. The range in diameter of these vesicles is from 0.25–1 μm. This procedure is well suited for entrapment for large molecules.

Smaller unilamellar vesicles can also be formed using a variety of techniques. By dissolving phospholipids in ethanol and injecting them into a buffer, the lipids will spontaneously rearrange into unilamellar vesicles. This provides a simple method to produce UVs which have internal volumes similar to that of those produced by sonication (0.2–0.5 L/mol/lipid). Sonication or extrusion (through filters) of MLVs also results in dispersions of UVs having diameters of up to 0.2 μm, which appear as clear or translucent suspensions.

Another common method for producing small UVs is the detergent removal technique. Phospholipids are solubilized in either ionic or non-ionic detergents such as cholates, Triton X, or n-alkylglucosides. The drug is then mixed with the solubulized lipid-detergent micelles. Detergent is then removed by one of several techniques: dialysis, gel filtration, affinity chromatography, centrifugation, or ultrafiltration. The size distribution and entrapment efficiencies of the UVs produced this way will vary depending on the details of the technique used. Also when proteins are entrapped, there is no certainty that once the detergent has been removed, the protein will renature into its native bioactive conformation.

The therapeutic use of liposomes includes the delivery of drugs which are normally very toxic in the free form. In the liposomal form the toxic drug may be directed away from the sensitive tissue and targeted to selected areas. Liposomes can also be used therapeutically to release drugs slowly, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body.

The route of delivery of liposomes can also affect their distribution in the body. Passive delivery of liposomes involves the use of various routes of administration, e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Many hydrophobic drugs, including cyclosporine, fall into this category because they cannot be easily dissolved in a water-based medium and must be dissolved in alcohols or surfactants which have been shown to cause toxic reactions in vivo. Liposomes, composed of predominantly lipids, with or without cholesterol are nontoxic. Furthermore, since liposomes are made of amphipathic molecules, they can entrap hydrophilic drugs in their interior space and hydrophobic molecules in their lipid bilayer.

For a variety of reasons, having to do primarily with the inability of those of ordinary skill to entrap sufficient cyclosporins in a stable liposomal carrier, a therapeutically effective cyclosporin intercalated liposome product has not been commercially available. It has thus been a desideratum to develop a liposomal cyclosporin containing a formulation which enables a high proportion of the active agent to be incorporated therein, and which is sufficiently stable for commercial purposes. This invention provides such a product.

SUMMARY OF THE INVENTION

A stable immunosuppressive formulation is prepared by hydrating a solid lipid phase comprising a negatively charged phospholipid and a cyclosporin with a physiologically compatible buffer, preferably an aqueous solution having a pH of from 7.0 to 9.5, preferably from 7.5 to 9.1. The solid lipid phase may be formed by dissolving the phospholipid and the cyclosporin in an organic solvent. A neutral phospholipid, such as a phosphatidylcholine, preferably those having lipid portions principally composed of straight 16 or 18 carbon fatty acid chains may also be included in the solid lipid phase. The negatively charged phospholipid is preferably a phosphatidylglycerol, preferably those having lipid portions principally composed of straight 14 to 18 carbon fatty acid chains, or a phosphatidic acid, for example, distearoylphosphatidylglycerol, dipalmitoylphosphatidylglycerol, dimyristoylphosphatidylglycerol, or dimyristoylphosphatidic acid.

More specifically, a stable liposomal cyclosporin therapeutic formulation is prepared by a process which comprises the steps of:

(a) dissolving (i) a phosphatidylcholine, (ii) a compound selected from the group consisting of a phosphatidylglycerol, phosphatidic acid, or mixtures thereof and (iii) a cyclosporin in an organic solvent to form a solution wherein the molar ratio of (i) to (ii) m (iii) ranges from about 7:7:0.05 to about 7:3:2.

(b) drying the organic solution thus formed to form a solid phase, e.g., a film or powder, (c) hydrating the solid phase with an aqueous solution having a pH from about 7.5 to about 9.5 to form the stable liposomal cyclosporin therapeutic formulation.

In another aspect, the invention is a therapeutic lipid composition comprising a negatively charged lipid and a cyclosporin, preferably cyclosporine, suspended in an aqueous solution having a pH ranging from about 7.5 to about 9.1.

In a preferred embodiment of the invention the liposomes are unilamellar vesicles having a diameter of less than 0.2 μm. Further, cholesterol may also be incorporated into the liposome, preferably in amounts up to 50 mole percent of the phosphatidylcholine, to acid stability to the liposome membrane.

The invention provides a novel process and a cyclosporine intercalated liposomal formulation which is stable on storage, contains a therapeutically effective amount of active ingredient, and provides a liposomal cyclosporine formulation having reduced toxicity. The process of the invention provides a commercially feasible process for the production of liposomal cyclosporine.

DETAILED DESCRIPTION OF THE INVENTION

Figure 1:
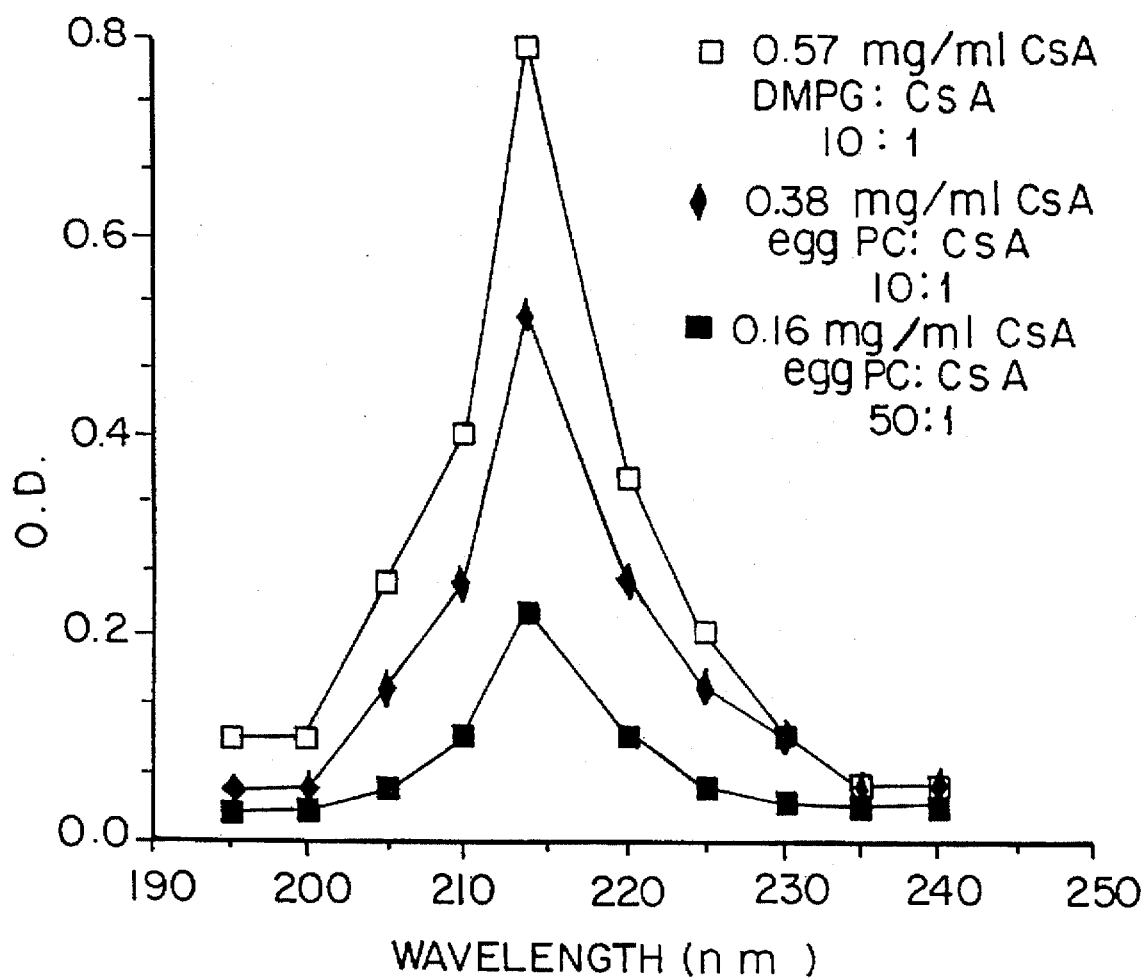
FIG. 1 is a graph depicting the results of tests used to determine a liposome formulation.

As used herein, the term liposome refers to unilamellar vesicles or multilamellar vesicles such as are described in U.S. Pat. Nos. 4,753,788 and 4,935,171, the contents of which are incorporated herein by reference. The term encapsulation, as used herein, refers to the incorporation of the cyclosporin into the liposome membrane.

The process of the present invention is initiated with the preparation of a solution from which the liposomes are formed. Briefly, a quantity of a phosphatidylcholine, a phosphatidylglycerol and cyclosporine is dissolved in an organic solvent, preferably chloroform, to form a solution. The solution is evaporated to form a solid lipid phase such as a film or powder, for example, with a rotary evaporator, spray dryer or other means. The film is then hydrated with an aqueous solution having a pH ranging from about 7.0 to about 9.5 to form a liposome dispersion.

Multilamellar liposomes are formed by agitation of the dispersion, preferably through the use of a thin-film evaporator apparatus such as is described in U.S. Pat. No. 4,935,171. Unilamellar vesicles are formed by the application of a shearing force to an aqueous dispersion of the lipid solid phase, e.g., by sonication or the use of a homogenizing apparatus such as a Gaulin homogenizer or a French press. Shearing force can also be applied using ether injection, freezing and thawing, dialyzing away a detergent solution from lipids, or other known methods used to prepare liposomes. The size of the liposomes can be controlled using a variety of known techniques including the duration of shearing force. Preferably, the modified Gaulin homogenizing apparatus described in U.S. Pat. No. 4,753,788 is employed to form unilamellar vesicles having diameters of less than 200 nanometers at a pressure of 7,000 to 13,000 psi and a temperature of about the aggregate transition temperature of the lipids. Methods for the agitation or shearing of lipids to form multilamellar or unilamellar vesicles are known in the art and are not part of this invention per se.

Distearoylphosphatidylcholine or egg phosphatidylcholine (egg PC) are preferred phosphatidylcholines for use in the invention. Suitable phosphatidylcholines include those obtained from soy beans or other plant sources, or those that are partially or wholly synthetic, such as dipalmitoylphosphatidylcholine. All of these are commercially available.

The preferred phosphatidylglycerols for use in the invention are distearoylphosphatidylglycerol (DSPG) and dimyristoylphosphatidylglycerol (DMPG). Other phosphatidylglycerols which are suitable for use include dilaurylphosphatidylglycerol (DLPG). All of these are commercially available.

Dimyristoylphosphatidic acid, distearoylphosphatidic acid, and dipalmitoylphosphatidic acid can be used in place of, or in addition to, the phosphatidylglycerol. The ingredients are preferably incorporated in solution in a molar ratio of phosphatidylcholine to phosphatidylglycerol or phosphatidic acid, to cyclosporine ranging from about 7:7:0.05 to about 7:3:2, most preferably 7:5:2. Other molar ratios such as 7:5:1 to 7:3:1 can also be used with substantially equivalent results.

The preferred organic solvent is chloroform, but other solvents or combinations of solvents, such as ether, methanol, ethanol and other alcohols can also be used.

The preferred aqueous solution for purposes of hydration is a buffered solution, e.g., 0.15M phosphate buffered saline (0.145M NaCl 0.003M $NaH_2PO_4$, 0.0035M $Na_2H_2PO_4$) (PBS), with a pH of 7.8.

The formulation produced in accordance with the above process entraps a high percentage of cyclosporine, 60% or more, and is stable on storage, which makes therapeutic use of the formulation commercially feasible. The formulation may also be lyophilized, stored and rehydrated without loss of efficacy. Since dosage regimens for free cyclosporine are well known to medical practitioners, the amount of the cyclosporine intercalated liposome formulation of the invention which is effective for the suppression of immune responses in mammals and particularly humans will be apparent to those of ordinary skill.

The encapsulation of cyclosporine in the manner described reduces the toxicity of existing therapeutic formulations and enhances its therapeutic effectiveness.

This invention will be more fully understood by reference to the following examples, which are intended to be illustrative of the invention, but not limiting thereof. Examples 1–6 detail the formation, and both chemical and biological testing of the liposomal cyclosporin of the invention.

EXAMPLE 1

A series of liposome formulations containing cyclosporine was prepared using the rotary evaporation technique, in which the lipids and cyclosporine were dissolved in an organic solvent (chloroform), and the solution thus formed was dried in a rotary evaporator. The dried film was then hydrated with an aqueous solution buffered to pH of 6.5 to 9.1 to form multilamellar vesicles.

Cyclosporine multilamellar vesicles (cyclosporine-MLVs) were prepared from cyclosporine powder (M.W.= 1201), dimyristoylphosphatidylglycerol (DMPG, M.W.= 684), and egg phosphatidylcholine (M.W.=786) in a 7:5:2 molar ratio. Stock solutions (10 mg/ml) of cyclosporine, DMPG and egg PC were prepared in chloroform.

Cyclosporine-MLVs were prepared by combining 1.20 ml of the cyclosporine stock solution, 2.75 ml of the egg PC stock solution and 1.70 ml of the DMPG stock solution in a 100 ml round bottom flask. The organic solvent, chloroform, was then evaporated by placing the round bottom flask on a rotary evaporator with a water bath temperature of 36° C. set at 95 rpm. The cyclosporine-MLVs were formed when 3.0 ml of sterile 0.01M PBS, pH 7.8, heated to 52° C., was added to the round bottom flask containing the drug-lipid film and placed in a heated shaker, set at 52° C., and rotated at 120 rpm for 20 minutes. A small, sterile magnetic stir bar was then added to the round bottom flask to help remove the film by stirring it vigorously (high setting) with low heat (60° C.), for about 5–10 minutes on a hot plate-stirrer. The cyclosporine-MLVs were transferred to a sterile test tube. An additional 2.0 ml of sterile PBS, pH 7.8, was added to the round bottom flask to rinse the flask of any remaining MLVs. The pooled MLVs were centrifuged at 2987×g for 20 minutes, the supernatant removed and the MLV pellet resuspended in 5.0 ml of sterile PBS, pH 7.8. The MLVs were recentrifuged at 2987×g for 20 minutes. After removal of the supernatant, the final MLV pellet was resuspended in 5.0 nil of sterile PBS, pH 7.8. Empty-MLVs (E-MLVs) were prepared at the same time as the cyclosporine-MLVs, using the same procedures as those described for the cyclosporine-MLVs, except with the deletion of the cyclosporine. In this procedure, liposomes were formed with the following components:

1. DMPG:cyclosporine 10:1 molar ratio;

2. egg PC:cyclosporine 10:1 molar ratio; and

3. egg PC:cyclosporine 50:1 molar ratio.

Each of the liposome samples was diluted 1:30 in methanol and spectrophotometric analysis was used to determine the concentration of cyclosporine, by obtaining the optical density (O.D.) at 214 nm using an extinction coefficient of 44,900.

The results are shown in FIG. 1, where it can be seen that a liposome formulation comprising DMPG:cyclosporine at a 10:1 molar ratio encapsulates 0.57 mg/ml cyclosporine, significantly higher than those liposomes formulated with egg PC.

EXAMPLE 2

Another series of multilamellar vesicle samples, i.e., liposomes, was prepared in accordance with the process set forth in Example 1. These samples were as follows:

1. egg PC:DMPG:cyclosporine 7:5:1 molar ratio

2. egg PC:DMPG:cyclosporine 3:3:1 molar ratio

3. egg PC:DMPG:cyclosporine 5:3:1 molar ratio

The MLV samples were diluted 1:30 in methanol and spectrophotometric analysis was used to determine the concentration of cyclosporine, by obtaining the O.D. at 214 nm using an extinction coefficient of 44,900.

Figure 2:
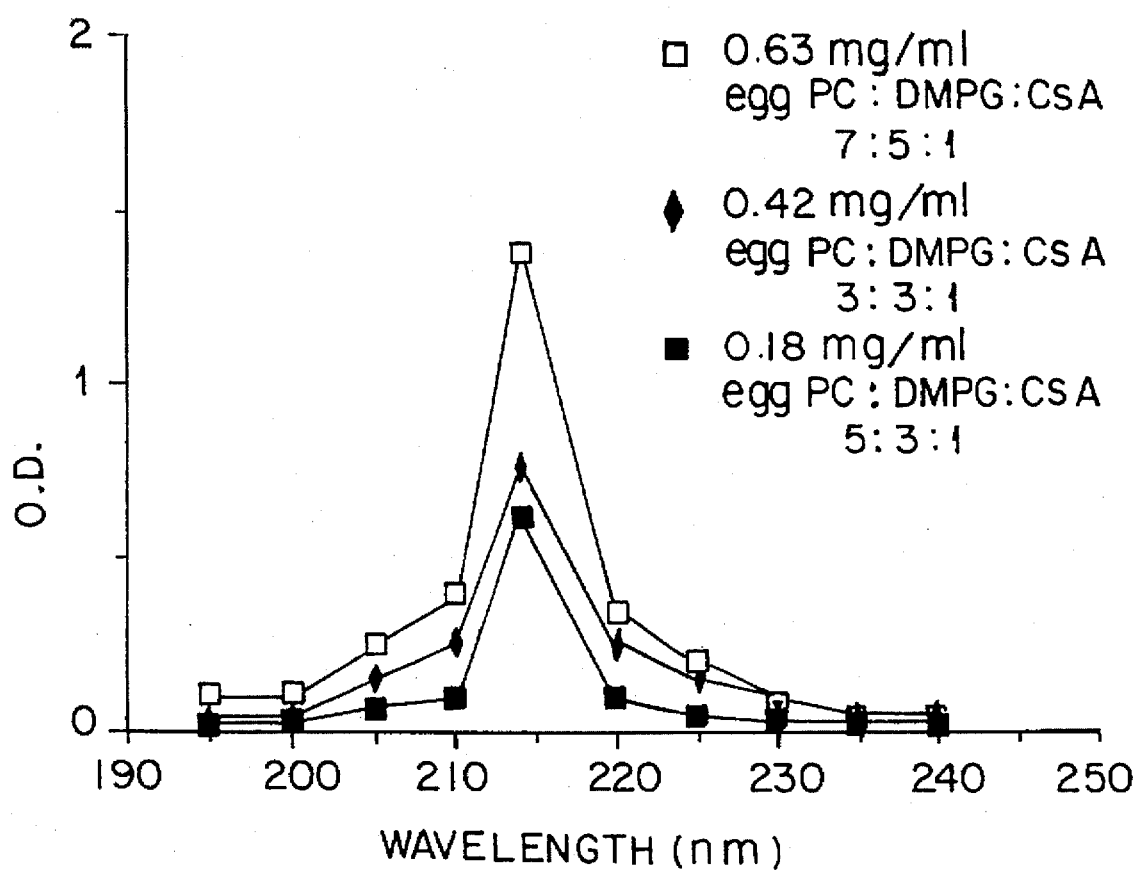
FIG. 2 is a graph depicting the results of tests used to determine the concentration of various components of a liposome formulation.

The results of the spectrophotometric analysis are shown in FIG. 2, where it can be seen that MLVs comprising egg PC:DMPG:cyclosporine in a 7:5:1 ratio encapsulated 0.63 mg/ml cyclosporine, significantly more than the same compositions at other molar ratios.

EXAMPLE 3

Another series of multilamellar vesicles was prepared in accordance with the process set forth in Example 1, varying the concentration of DMPG. The samples were as follows:

1. egg PC:DMPG:cyclosporine 7:5:1 molar ratio

2. egg PC:DMPG:cyclosporine 7:7:1 molar ratio

3. egg PC:DMPG:cyclosporine 7:3:1 molar ratio

4. egg PC:DMPG:cyclosporine 7:1:1 molar ratio

Figure 3:
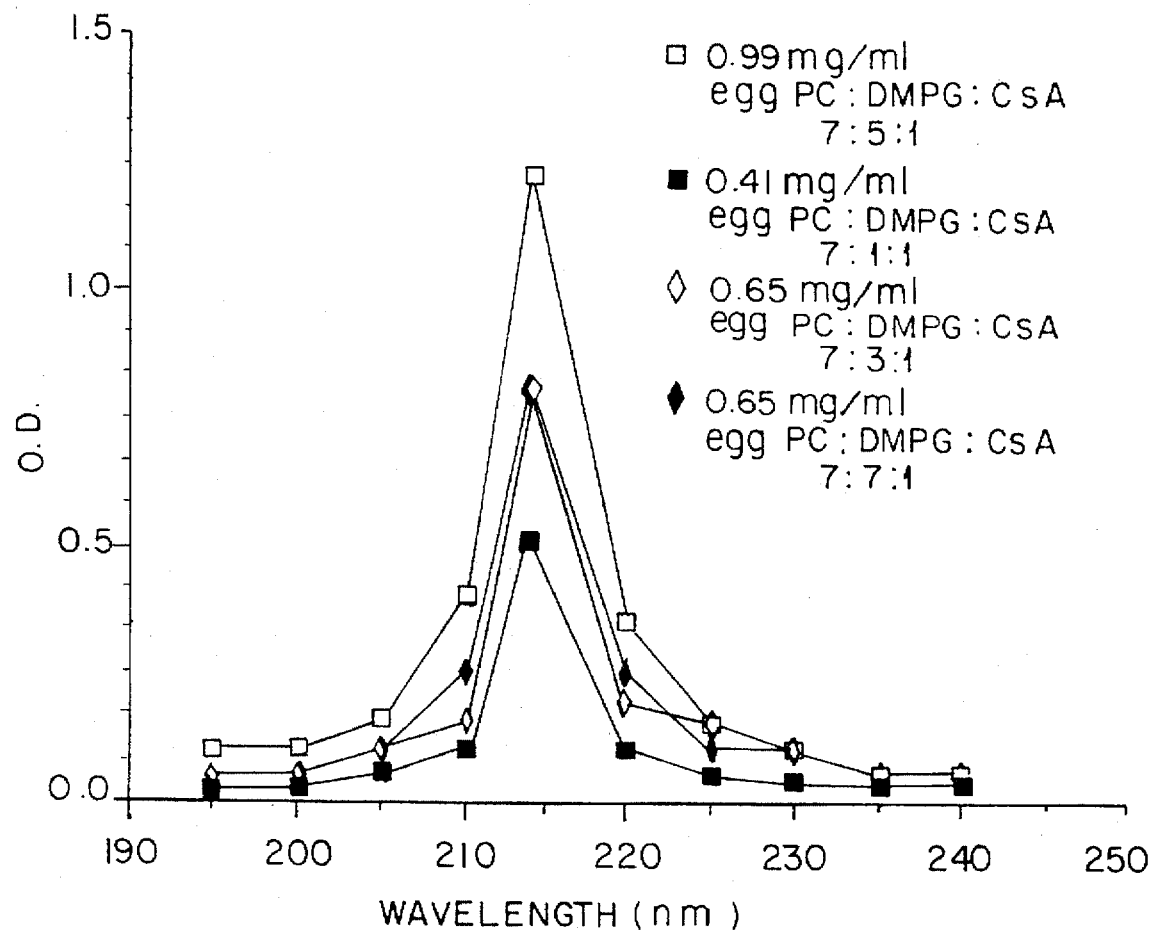
FIG. 3 is a graph depicting the results of tests used to determine molar ratios of DMPG in a liposome formulation.

The samples were diluted 1:30 in methanol and the concentration of cyclosporine determined as in the previous examples. The results of the spectrophotometric analysis are shown in FIG. 3, in which it is seen that MLVs having an egg PC:DMPG:cyclosporine molar ratio of 7:5:1 encapsulate a significantly greater mount of cyclosporine (0.99 mg/ml) than do MLVs containing DMPG at lower or higher quantities.

EXAMPLE 4

Another series of MLVs was prepared in accordance with the process set forth in Example 1. In this series the concentration of cyclosporine was varied, as follows:

1. egg PC:DMPG:cyclosporine 7:5:1 molar ratio

2. egg PC:DMPG:cyclosporine 7:5:2 molar ratio

3. egg PC:DMPG:cyclosporine 7:5:0.5 molar ratio

The foregoing samples were diluted 1:30 in methanol and spectrophotometric analysis was used to determine the concentration of cyclosporine, by obtaining the O.D. at 214 nm using an extinction coefficient of 44,900.

The analysis results are shown in Table 1. As seen, the percent of cyclosporine encapsulated was essentially the same at all three molar levels.

TABLE 1

Encapsulation with Varying Molar Ratios of Cyclosporine

| Lipid:Drug Ratio | O.D. @ 214 nm | Total Cyclosporine | Recovered Cyclosporine | Percent Encapsulation |
|---|---|---|---|---|
| 7:5:0.5 | 0.36 | 0.6 mg | 0.26 mg | 43% |
| 7:5:1 | 0.78 | 1.2 mg | 0.57 mg | 47% |
| 7:5:2 | 1.38 | 2.4 mg | 1.01 mg | 42% |

EXAMPLE 5

Another series of liposomes was prepared in accordance with the process set forth in Example 1. In this series, a 7:5:2 egg PC:DMPG:cyclosporine molar ratio was used for all liposomes. However, the rehydration buffer pH was varied between values of from 6.5 and 9.1.

The samples were then diluted 1:30 in methanol and the concentration of cyclosporine again determined by spectrophotometric analysis at 214 nm using an extinction coefficient of 44,900.

The results are shown in Table 2, where it is seen that the optimum buffer pH in terms of % drug recovery is 7.8, although satisfactory results are achieved at pH values ranging from 7.2 to 9.1.

TABLE 2

Effect of pH on Encapsulation Efficiency

| pH | 6.5 | 7.2 | 7.5 | 7.8 | 8.2 | 9.1 |
|---|---|---|---|---|---|---|
| % cyclosporine encapsulation (recovery of initial drug) | 28.7 | 66.0 | 71.7 | 88.0 | 77.0 | 72.3 |
| % standard deviation | 5.5 | 3.0 | 2.9 | 6.0 | 3.0 | 2.0 |
| range % encapsulation | 23.2–34.2 | 63–69 | 68.8–74.6 | 8 2–74–94 | 2 70.3–80 | 74.3 |

From the results set forth in the foregoing examples, it is apparent that a liposome formulation comprising egg PC:DMPG:cyclosporine in a 7:5:0.05 to 7:5:2 molar ratio is far more effective in encapsulating cyclosporine during the process of formation than prior art formulations. For optimum results, it is essential that hydration be undertaken in a medium having a pH of from about 7.0 to about 9.5, preferably 7.8.

The stability of the formulations of this invention is demonstrated by the following example.

EXAMPLE 6

This experiment was used to show the effect of different temperatures (4° C. 25° C. and 37° C.) for varying periods of time (2 hrs, 24 hrs, 48 hrs) on cyclosporine-MLV association when the cyclosporine-MLVs were freshly prepared or rehydrated following lyophilization Cyclosporine intercalated MLVs were prepared with a molar ratio of 7:5:2, egg PC:DMPG:cyclosporine, using the technique of roto-evaporation described previously. The hydrating buffer was PBS, pH 7.8. Following hydration, the MLVs were layered onto a G50–80 Sephadex column in a 5 ml syringe and centrifuged at 2500 rpm for 10 minutes. This was done to separate unencapsulated cyclosporine from cyclosporine intercalated MLVs.

Following centrifugation, cyclosporine-MLV pellets were resuspended in PBS, pH 7.8 and pooled to give a total volume of about 9 ml. The pooled sample was checked for cyclosporine concentration by ultraviolet absorbance spectrophotometry. The total sample volume was then split into two fractions of 4.5 ml each. One fraction was further subdivided into three more aliquots (1.5 ml per aliquot). The other fraction was frozen to −70° C. for at least 2 hours and then lyophilized.

The unfrozen aliquots (15 ml each), containing the fresh cyclosporine-MLVs, were incubated at either 4° C., 25° C. (room temperature) or 37° C., and samples (0.5 ml) were removed from each temperature condition at 2 hours, 24 hours, and 48 hours. Upon removal, each sample was centrifuged through a Sephadex G50–80 column in a 5 ml syringe, the cyclosporine-MLV pellet resuspended, and analyzed for cyclosporine concentration.

The lyophilized cyclosporine-MLVs were rehydrated with enough sterile deionized water to return the preparation to the original volume. The rehydrated material was analyzed for cyclosporine concentration and then divided into three 1.5 ml aliquots which were stored at 4° C., 25° C. (room temperature) or 3° C. Samples (0.5 ml) were removed from each storage condition after 2 hours, 24 hours and 48 hours, centrifuged through a Sephadex G50–80 column in a 5 ml syringe and each cyclosporine-MLV pellet resuspended and analyzed for cyclosporine concentration. The results are summarized in Tables 3 and 4.

TABLE 3

Fresh Cyclosporine-MLVs

| Storage Temperature | Time | Conc.(mg/ml) | % of Initial Drug Conc. |
|---|---|---|---|
| 4° C. | 0 | 0.69 | — |
| 4° C. | 2 h | 0.55 | 80% |
| 4° C. | 24 h | 0.56 | 81% |
| 4° C. | 48 h | 0.56 | 81% |
| 25° C. | 0 | 0.69 | — |
| 25° C. | 2 h | 0.45 | 65% |
| 25° C. | 24 h | 0.48 | 70% |
| 25° C. | 48 h | 0.48 | 70% |
| 37° C. | 0 | 0.69 | — |
| 37° C. | 2 h | 0.45 | 65% |
| 37° C. | 24 h | 0.48 | 70% |
| 37° C. | 48 h | 0.23 | 33% |

TABLE 4

Lyophilized and Rehydrated Cyclosporine-MLVs

| Storage Temperature | Time | Conc.(mg/ml) | % of Initial Drug Conc. |
|---|---|---|---|
| 4° C. | 0 | 0.59 | — |
| 4° C. | 2 h | 0.50 | 85% |
| 4° C. | 24 h | 0.49 | 83% |
| 4° C. | 48 h | 0.43 | 73% |
| 25° C. | 0 | 0.59 | — |
| 25° C. | 2 h | 0.44 | 75% |
| 25° C. | 24 h | 0.45 | 76% |
| 25° C. | 48 h | 0.44 | 75% |
| 37° C. | 0 | 0.59 | — |
| 37° C. | 2 h | 0.43 | 73% |
| 37° C. | 24 h | 0.40 | 68% |
| 37° C. | 48 h | 0.26 | 44% |

The data demonstrate similar results for both freshly prepared and lyophilized, rehydrated cyclosporine-MLVs indicating that the process of lyophilization and rehydration did not significantly alter the association of the cyclosporine with the MLVs. Both types of preparations exhibited some drug loss after 2 h incubation at all temperatures tested. However, when the preparations were stored at 4° C. for 2 h, the association of cyclosporine with the MLVs (15%–20% drug loss) was better than storage at either 25° C. or 37° C. (25%–35% drug loss).

In producing a cyclosporine-MLV formulation which was stable and demonstrated optimum drug encapsulation, several factors were examined, including various lipids, their molar ratios, and the pH of the hydration buffer. Since cyclosporine is a hydrophobic molecule and will become incorporated into the lipid membrane rather than the aqueous space within the liposome, a multilamellar vesicle was chosen for initial experiments to maximize the lipid volume per vesicle.

The first studies were done using one lipid with cyclosporine. DMPG:cyclosporine MLVs showed considerably higher encapsulation than egg PC:cyclosporine MLVs. This may have been due to the flexibility of DMPG at its transition temperature, approximately 23° C. (room temperature), which enables it to accommodate a large molecule like cyclosporine in the liposome bilayer. Non-hydrogenated egg was used because egg PC, unlike synthetic lipids, containing more than one lipid, each with different chain lengths, which may also help accommodate the large cyclosporine molecule within the liposome bilayer.

When various combinations of the lipids, egg PC and DMPG, were used to optimize cyclosporine incorporation into liposomes and minimize its leakage from the MLVs, a molar ratio of 7:5:1 of egg PC:DMPG:cyclosporine showed the highest amount of drug encapsulation. This suggests that at the proper ratio, the properties of both lipids contribute to an increased encapsulation efficiency.

To further study the association of cyclosporine with the negatively charged DMPG in the liposome membrane, investigations were done to examine the effect of varying the hydrating buffer pH on cyclosporine liposome incorporation. Maximum encapsulation is observed with 0.15M PBS, pH 7.8; modifying the pH above or below this number further alters the encapsulation efficiency. Using a hydrating buffer with a pH between 6.5 and 9.5 yields drug recoveries ranging from 25 to almost 88%.

The final formulation studies were done using increased mounts of cyclosporine in the liposome formulation to decrease the lipid to drug ratio. These studies showed that a 2-fold increase in the molar ratio of cyclosporine (7:5:2 molar ratio, egg PC:DMPG:cyclosporine) did not alter the percentage of initial drug recovered in the liposomes. This is important because more cyclosporine-MLVs could be made with less lipid, decreasing the cost and time needed to produce a given amount of encapsulated drug.

Tests were undertaken to determine the therapeutic efficacy of the cyclosporine liposomal formulations of the invention. The materials and methods are described in the following sections and the tests are detailed in Examples 7–12.

Preparation of Drug Formulations for Treatment of Mice

Free cyclosporine (cyclosporine-CreL) was prepared by dissolving 12 mg of cyclosporine powder in 1.0 ml of Cremophor-eL with 0.1 ml of 95% ethanol and then heating to 50° C. After the cyclosporine had dissolved, 1.9 ml of sterile 0.15M PBS, pH 7.8, heated to 55° C., was added to the solution, resulting in a cyclosporine concentration of 4 mg/ml. The PBS used had the following composition: 0.0028M monosodium phosphate, 0.0072M disodium phosphate and 0.145M sodium chloride. The solution was further diluted with PBS to give a final cyclosporine concentration of 2.0 mg/ml. To 1.0 ml of the 2.0 mg/ml cyclosporine solution, 9.0 ml of sterile 0.15M PBS, pH 7.8, was added resulting in a cyclosporine concentration of 0.2 mg/ml. Three different concentrations of cyclosporine solution were then prepared since the doses required by the mice varied, and it was necessary to keep the volume of injected material similar for all treatments (between 0.1 to 0.2 ml).

Cyclosporine-MLVs and E-MLVs were prepared as described in the second paragraph of Example 1. The concentration of cyclosporine in the cyclosporine-MLV suspension was determined in Examples 7–12 by using the Beers-Lambert equation and the extinction coefficient for cyclosporine at 238 nm when the drug was dissolved in methanol and tetrahydrofuran (THF), v/v, 1:1. The cyclosporine was extracted from the cyclosporine-MLVs by adding 0.1 ml of cyclosporine-MLV sample to a test tube containing 1.4 ml of absolute methanol. The test tube was vortexed for about 10 seconds, 1.5 ml of THF added and the solution was vortexed again. The E-MLV sample was processed similarly. This extraction procedure resulted in a 1:30 dilution of the cyclosporine-MLV sample and was assayed spectrophotometrically at 238 nm, referenced against a 1:30 dilution of the E-MLV sample. After the cyclosporine concentration was determined, 1 to 2 ml aliquots of cyclosporine-MLVs were frozen slowly to −70° C. in a Revco freezer. When the samples were completely frozen, they were lyophilized and stored at −20° C. Prior to use, they were resuspended in sterile distilled water, heated to 37° C. for 10 minutes, and re-assayed for cyclosporine concentration. If necessary, the sample was diluted with sterile PBS, pH 7.8, to achieve the appropriate concentration for injection.

Animal Model for Cyclosporine Treatments

The mice used in these experiments were C57BL/6J female mice, 8 to 16 weeks old. The mice were inoculated intravenously with various doses of cyclosporine-MLVs and cyclosporine-CreL, at different times, depending upon the therapeutic regimen. On the day of sacrifice, blood was aseptically removed either by cardiac puncture or by retroorbital bleeding. The serum was collected and stored at −20° C. for future hemagglutination assays and Blood Urea Nitrogen (BUN) determinations. Some kidneys were removed and fixed in a 10% formalin solution, pH 7.3, diluted with 0.15M PBS and stored at 4° C. until sectioned. The spleens were also aseptically removed and homogenized in sterile tissue homogenizers. The spleen homogenates from each treatment group were pooled, diluted to 6.0 ml with RPMI 1640 and layered over 4.0 ml of Neutrophil Isolation Medium in a 15 ml sterile conical centrifuge tube. The material was centrifuged at 225×g for 30 minutes at 18°–20° C. The separated lymphocyte band was removed from the NIM gradient and diluted with 6.0 ml of RPMI. The cells in this band were centrifuged at 125×g for 9 minutes, the supernatant discarded, the pellet resuspended in 6.0 ml of RPMI and again centrifuged at 125×g for 9 minutes. The supernatant was again discarded and the final pellet resuspended in 1.0 ml of RPMI. The cell concentration and viability of this final pellet was determined by counting the cells stained with 0.1% Trypan blue with a hemacytometer counting chamber. The concentration was adjusted to $5 \times 10^6$ cells/ml with complete RPMI (RPMI with 10% newborn calf serum, 2% penicillin—streptomycin and glutamine). This cell suspension was then used for the modified Jerne Plaque assay and the T-lymphocyte blastogenesis assay.

Kennedy Assay; Modified Jerne Plaque Assay

A 1:5 dilution of guinea pig complement was prepared by diluting the complement with magnesium saline; a $5 \times 10^5$ lymphocyte suspension was made by diluting the $5 \times 10^6$ cell suspension 1:10 with magnesium saline. A 1% sheep red blood cell (sRBC) suspension containing 1:10 dilution of complement was prepared by mixing 1.0 ml of 2% sRBC with 1.0 ml of a 1:5 dilution of complement.

The Kennedy assay (Kennedy, 1971) was set up in a 96 well flat bottom tissue culture dish and each lymphocyte sample from a given treatment group was tested in triplicate. To each well was added, 0.1 ml of the lymphocyte suspension in complete RPMI tissue culture medium ($5 \times 10^5$ cells/ml), 0.05 ml of 1% sRBC with 1:10 complement, and 0.1 ml of complete RPMI. Some of the control wells contained 0.1 ml of the lymphocyte suspension, 0.05 ml of 1% sRBC without complement and 0.1 ml of complete RPMI. Two additional control wells were prepared by mixing 0.05 ml of 1% sRBC and 0.2 ml of complete RPMI in one well and mixing 0.05 ml of 1% sRBC with 1:10 complement with 0.2 ml of RPMI in another well. The culture dish was then placed in a humidified environment (tray lined with a moistened paper towel) and incubated at 4° C. for 1.25 hours. The culture dish was then placed at room temperature for 20 minutes and incubated for 1.5 hours in a 37° C., 5% $CO_2/95\%$ air incubator. Following the last incubation, plaque formation was evaluated by counting the plaques in each well with an inverted microscope at 400×, and averaging the number of plaques in three wells for each sample. Results are reported as plaque forming units (PFU)/$10^6$ cells.

T-Lymphocyte PHA Stimulation and Chemotaxis Assay

Blastogenesis of the T-lymphocytes was done in a 96 well, round bottom, tissue culture dish. To each well was added 0.1 ml of a $5 \times 10^6$ cells/ml lymphocyte suspension (isolated for the Kennedy assay), prepared from each treatment group. Cell suspension samples from each treatment group were done in duplicate. To each of the test wells 0.1 ml of a 900 µg/ml solution of phytohemagglutinin (PHA) diluted in RPMI 1640 and 0.05 ml of complete RPMI 1640 were added. Control wells confined 0.1 ml of lymphocyte suspension and 0.15 ml of complete RPMI. The tissue culture dish was then incubated for 60 hours in a 5% $CO_2$/95% air, 37° C. incubator. After the 37° C. incubation period, the material from each well was pipetted into a microfuge tube and centrifuged at 8320×g for 10 minutes. Each supernatant from this centrifugation was pipetted into another microfuge tube and kept frozen at −20° C. until it was used in the chemotaxis assay.

Microscope slides were acid washed in a 2:1 ratio of 3M HCl and 95% ethanol for 2 hours, rinsed with deionized water and soaked in 0.5% gelatin for 5 minutes to reduce any negative charge. The slides were rinsed a final time with distilled water and allowed to air dry. Agarose for the slides was prepared by dissolving 1.0 g of agarose and 0.25 g gelatin in 50 ml of distilled water. This preparation was autoclaved, cooled to 47° C., mixed with 50 ml of warmed RPMI1640 and approximately 3 ml of this solution pipetted onto each glass slide. After the agarose had solidified, a row of three wells were made in the agarose of each slide.

Macrophages were isolated from the spleen homogenates of nondrug-treated C57BL/6J mice using the NIM separation technique since macrophages will localize in the mixed lymphocyte band of this gradient. The lymphocyte/monocyte suspension was then adjusted to $3 \times 10^7$ cells/ml in complete RPMI 1640. The three wells in the agarose on each slide were then filled as follows: 15 µl of $3 \times 10^7$ cells/ml in the center well, 15 µl of RPMI in one outer well and 15 µl of a blastogenesis supernatant sample in the other outer well. The slides were placed in a sterile humidified chamber (sterile petri dish lined with moistened, sterile filter paper) and incubated in a 5% $CO_2$/95% air, 37° C. incubator for 18 hours. After incubation, the slides were fixed by immersion in absolute methanol for 30 minutes, and then for 30 minutes in 37% formaldehyde, pH 7.3; the agarose was then carefully removed from the slides. The slides were stained with Wright Stain and evaluated for macrophage migration by examining them with a microprojector and measuring cell migration from the edge of the well.

Hemagglutination Assay of Serum from SRBC Stimulated Mice

Serum samples obtained from each mouse were used to prepare 2-fold serial dilutions (1:1 to 1:1024) in 0.15M PBS, pH 7.3. The assay was performed in a 96 well, round bottom tissue culture plate. Into each test well was placed 0.05 ml of 0.5% sRBC ($1 \times 10^6$ cells/ml) and 0.05 ml of serum sample; control wells contained 0.05 ml of 0.5% sRBC and 0.05 ml of 0.15M PBS, pH 7.3. The plate was placed on a shaker and rotated at 100 rpm for 10 minutes, followed by a one hour incubation at room temperature. The hemagglutination titer for each sample was determined by examining the wells through an inverted microscope at 400×.

Hemagglutination Assay of Serum from LPS Stimulated Mice

A sRBC suspension bound with Lipopolysaccharide (LPS) was prepared as described by Andersson (1971). LPS from *Salmonella abortus equi* was dissolved in sterile 0.15M PBS, pH 7.3, at a concentration of 1.0 mg/ml. The LPS (3.0 ml) was then boiled in a glass screw cap tube for two hours. After heating, the LPS was cooled to 37° C. in a water bath and 1.0 ml of packed sRBC added to the LPS, followed by an additional incubation at 37° C. for 45 minutes. The sRBC-LPS mixture was then washed three times in 0.15M PBS, pH 7.3, and diluted to $1 \times 10^7$ cells/ml. The serum samples for the assay were prepared by making two-fold dilutions of each sample with 0.15M PBS, pH 7.3, from 1:1 to 1:2048. The assay was performed as described above, except that the sRBC-LPS suspension replaced the 0.5% sRBC.

Histology of Mouse Kidneys Following Cyclosporine Treatment

After setting in buffered formalin for at least 72 hours at 4° C., the kidneys were further fixed as follows: 2 hours in 70% ethanol; 15 hours in 80% ethanol; 1.5 hours in 90% ethanol; three incubations for 1.5 hours each in 100% ethanol; two incubations for 15 hours each in dehydrant; and three incubations for 1.5 hours each in paraffin. The kidneys were embedded in paraffin and 6 µm sections were obtained. The sections were stained as follows: two immersions in dehydrant for 2.5 minutes each time, twice in 100% ethanol for 2 minutes each time, 95% ethanol for 2 minutes, 70% ethanol for 2 minutes, rinse in water, immersion in hematoxylin for 2.5 minutes, rinsed in water for 2 minutes, rinsed in acid-alcohol until the hematoxylin stopped leaching out, rinsed in water again, dipped 10 times in ammonium water, rinsed in water, eosin stained for 1.5 minutes, dipped 10 times in 95% ethanol, twice in 100% ethanol, and twice in dehydrant. Kidney sections were evaluated for nephrotoxicity by microscopically examining the sections at 100× and 400×.

In Vitro Antifungal Effects of Cyclosporine

Three species of Aspergillus, *A. fumigatus*, *A. flavus*, and *A. niger* and the yeast *Cryptococcus neoformans* were used in this portion of the study. These cultures were from the California State Polytechnic University, Pomona, microbiology culture collection and designated laboratory strains #385, #359, #360, and #608, respectively.

The culture medium used for growing these organisms was Sabouraud (SAB) dextrose broth and SAB dextrose agar (1.5%). The four species of fungi used in these studies were maintained on SAB agar slants. The Aspergillus cultures were transferred every 48 hours over a period of 6 days before spores were collected for testing. The spores were collected by washing the slant with 1.5 ml of sterile 0.85% saline. The spores were counted using a hemacytometer counting chamber and the number of spores adjusted to $1 \times 10^3$ spores/ml in 0.85% saline. The *C. neoformans* yeast cells were also transferred every 48 hours over a period of 6 days before collection; however, the cells were collected using SAB broth. The yeast cells were also counted using a hemacytometer counting chamber and the number of cells adjusted to $1 \times 10^3$ cells/ml in SAB broth.

To determine the antifungal activity of cyclosporine-CreL and cyclosporine-MLVs, SAB plates were seeded with drug-treated spores (or yeast cells) as follows: 0.15 ml of $1 \times 10^3$ spores/ml suspension was mixed in a test robe with the appropriate concentration of cyclosporine-MLVs or cyclosporine-CreL (1 µg, 5 µg, 10 µg, or 200 µg) and enough SAB broth was added to each tube containing different drug concentrations to attain a final volume of 0.5 ml in each robe; every robe was then vortexed and poured onto a separate SAB plate, being evenly distributed with a sterile bent glass rod; after 36 hours of incubation at 37° C., the colonies were counted and their diameters measured.

EXAMPLE 7

To determine if encapsulation of cyclosporine within MLVs altered its antifungal in vitro activity, studies were done to compare the in vitro antifungal effects of cyclosporine-MLVs and cyclosporine-CreL on the yeast, *Cryptococcus neoformans* and the molds, *Aspergillus flavus, fumigatus* and *niger*. Both the encapsulated (cyclosporine-MLV) and the unencapsulated (cyclosporine-CreL) inhibited the number of *C. neoformans* colonies in vitro after 36 hours of incubation. A concentration of 1 µg cyclosporine-MLV inhibited the yeast by 50% and 1 µg cyclosporine-CreL reduced the number by 65% relative to control, untreated samples. With increasing cyclosporine-MLV or cyclosporine-CreL concentrations (5 µg, 10 µg, and 200 µg) there was a further decrease in colony counts of 38, 10 and 2 for cyclosporine-MLVs and 3, 3, and 0 for cyclosporine-CreL compared to a colony count of 106 for control, untreated samples. Cyclosporine also affected the colony size of *C. neoformans*. When the yeast was exposed to cyclosporine-CreL, even at concentrations as low as 1 µg, there was a decrease in size of 87% compared to control, untreated samples. A similar degree of inhibition of yeast colony size was seen when 5 µg or 10 µg of cyclosporine-CreL was used; no detectable yeast was observed when the yeast was challenged with 200 µg of the drug. In contrast, inhibition of yeast colony size in the presence of varying amounts of cyclosporine-MLVs demonstrated a dose response; at 1 µg, 5 µg, 10 µg and 200 µg the colony sizes were 33%, 67%, 80% and 93%, respectively, compared to the control.

Although cyclosporine, in either form, did not reduce the number of Aspergillus spp. colonies, it did, however, inhibit the colony size of *A. flavus, A. fumigatus* and *A. niger*. The cyclosporine-MLVs reduced the colony size of *A. flavus* at concentration of 1 µg, 5 µg, 10 µg, and 200 µg by 50%, 78%, 92% and 96%, respectively, relative to the control, untreated culture. The cyclosporine-CreL, however, showed more marked inhibition of *A. flavus* than the cyclosporine-MLVs since it reduced the colony size, relative to controls, by 60% for 1 µg, 85% for 5 µg, 96% for 10 µg and 98% for 200 µg.

The cyclosporine-MLVs did not inhibit the colony size of *A. fumigatus* at concentrations of 1 µg and 5 µg but at 10 µg and 200 µg, the drug inhibited the fungus by 40% and 96%, respectively, relative to the controls. In contrast, cyclosporine-CreL inhibited the colony size of *A. fumigatus* at 5 µg, as well as at the higher doses of 10 µg and 200 µg, with reductions of 30%, 80% and 96%, respectively, compared to the untreated control.

The colony size of *A. niger* was reduced by both cyclosporine-MLVs and cyclosporine-CreL. Cyclosporine-MLVs reduced the colony size by 37%, 75%, 75% and 97.5%, relative to controls, at concentrations of 1 µg, 5 µg, 10 µg, and 200 µg, respectively. The cyclosporine-CreL showed greater inhibition since 1 µg, 5 µg, and 10 µg reduced the colony size by 87.5%, 87.5% and 92.5%, respectively, compared to the untreated controls. At 200 µg, inhibition of fungal growth was comparable for both forms of the drug.

These data indicate that encapsulation of cyclosporine into MLVs reduces the in vitro antifungal efficacy of the free drug for certain fungi when administered at doses of 10 µg or less. Higher drug levels (i.e., 200 μg of either form of the drug) have comparable in vitro antifungal activity.

EXAMPLE 8

To determine if cyclosporine-MLVs and cyclosporine-CreL had comparable immunosuppressive activity in vivo, C57BL/6J mice were treated with either form of the drug in conjunction with a T-dependent antigenic challenge of sRBC. The B-cell activity of these mice towards this antigen was then monitored by Jerne plaque assays and serum hemagglutinating antibody titres. In the first set of experiments, mice were treated 5 times with varying dose levels of the drug. The results of the Jerne plaque assay showed that mice challenged with sRBC, but not treated with cyclosporine, had a plaque forming unit value (PFU) of $560/10^6$ cells. When mice given sRBC were treated with Empty-L, however, there was a 1.4-fold increase in PFU compared to the untreated, antigen challenged mice. The mice treated with 5 doses of 5, 15, or 25 mg/kg of cyclosporine-CreL showed a reduction in plaques of 25%, 57%, and 84%, respectively, compared to the sRBC challenged, untreated controls. Mice treated with 1, 5, 15, or 25 mg/kg of cyclosporine-MLVs showed a reduction in plaques by 45%, 54%, 68%, and 89%, respectively, of that of the sRBC challenged, untreated controls. The plaque levels of mice treated with five doses of 5 mg/kg (total=0.55 mg per mouse) cyclosporine-MLVs were comparable to those of mice treated with five doses of 15 mg/kg (total=1.65 mg per mouse) cyclosporine-CreL.

Mouse serum from the above experiment was analyzed for hemagglutinating antibody titers. Non-antigen challenged, untreated mice had a hemagglutinating titer of 0. The mice given just sRBC, sRBC and CreL or sRBC and empty-L had titers of 1:853. The mice given sRBC and either 5 or 25 mg/kg cyclosporine-CreL showed a reduction in antibody titer of 80% and 99.5%, respectively, compared to mice given just sRBC. The mice treated with 1, 5, 15, or 25 mg/kg cyclosporine-MLVs showed a 97.5%, 99.5%, 99.5%, and 99.8% decrease, respectively, in antibody titer relative to the mice given only sRBC. Thus, mice treated with cyclosporine-MLVs had lower antibody titers compared to mice given comparable doses of cyclosporine-CreL The results also showed that neither CreL treatment nor empty-L treatment altered the antibody response of these mice to sRBC.

The T-cells from the mice treated with 5 doses of either cyclosporine-CreL or cyclosporine-MLVs were stimulated with PHA following their isolation. Their ability to produce the lymphokine, chemotaxin, was measured by a chemotaxin assay and expressed as a chemotactic index. The nonocyclosporine treated mice had a chemotactic index of 1.43. Mice treated with 5, 15, or 25 mg/kg cyclosporine-CreL showed reduced chemotaxin production as indicated by a reduction in the chemotactic index by 3%, 37%, and 50% compared to untreated, control mice. Mice treated with 5, 15, or 25 mg/kg cyclosporine-MLVs had chemotaxin indices reduced by 36%, 44%, and 38.5%, respectively, compared to untreated mice. Thus mice given only 5 mg/kg cyclosporine-MLVs showed suppression of chemotaxin production comparable to that of mice treated with 15 mg/kg cyclosporine-CreL.

EXAMPLE 9

In a next set of experiments, the immunosuppressive effect of lower total doses of cyclosporine-CreL and cyclosporine-MLVs was examined. In these in vivo experiments the mice were treated with 3 doses of either cyclosporine-MLVs or cyclosporine-CreL. The results from the Jerne plaque assay showed that sRBC-challenged mice given no cyclosporine had plaque levels of 680 PFU $10^6$ cells. Mice given sRBC and CreL also showed high numbers of plaques (700), but sRBC-challenged mice treated with 3 doses of 5 mg/kg (total=0.33 mg per mouse) or 15 mg/kg (total=0.99 mg per mouse) cyclosporine-CreL had plaque levels reduced by 50% (340) and 68% (220), respectively, compared with the non-cyclosporine treated mice. Mice treated with sRBC and 3 doses of either 5 mg/kg (total=0.33 mg per mouse) or 15 mg/kg (total=0.99 mg per mouse) cyclosporine-MLVs were more immunosuppressed in their sRBC response (70% (200) and 79% (140) reduction, respectively) than mice treated with comparable doses of cyclosporine-CreL.

When the mouse sera from the above experiment were assayed for hemagglutinating antibody titers, similar results to those seen for the Jerne plaque assay were obtained, as seen in Table 5.

TABLE 5

Antibody Titer (sRBC Challenge) with Three Doses

| DRUG TREATMENT (serum collected day 9) | TITER |
|---|---|
| G1: Control (sRBC only) | 1:853 |
| G2: 5.0 mg/kg cyclosporine-CreL | 1:341 |
| G3: 15.0 mg/kg cyclosporine-CreL | 1:128 |
| G4: 5.0 mg/kg cyclosporine-MLVs | 1:128 |
| G5: 15.0 mg/kg cyclosporine-MLVs | 1:43 |

In the testing reported in Example 9, C57BL/6J mice were inoculated with 0.2 ml of 10% sRBC IP on days 0 and 4. The mice were also treated with 3 intravenous doses (days 0, 4 and 8) of cyclosporine-CreL or cyclosporine-MLVs. Control mice G1 were inoculated with sRBC only. All mice were sacrificed on day 9 and a hemagglutination assay was done on sera pooled from 5 mice/group. Results are from 3 repetitions of 5 mice/group and are reported as the mean titer.

The mice given just sRBC had titers of 1:853 whereas mice treated with sRBC and either 5 or 15 mg/kg cyclosporine-CreL showed a 23-fold or 6.7-fold decrease in titer, respectively, compared to the non-cyclosporine treated mice; mice treated with sRBC and either 5 or 15 mg/kg cyclosporine-MLVs showed a 6.7-fold and 19.8-fold decrease, respectively. Comparable immunosuppression of the sRBC response was seen in mice given 5 mg/kg cyclosporine-MLVs and 15 mg/kg cyclosporine-CreL.

When the T-cells from mice treated three times with cyclosporine were stimulated with PHA and tested for chemotaxin production, chemotactic indices could be calculated to measure T-cell activity, as seen in Table 6.

TABLE 6

Chemotaxin Production of PHA-Stimulated T-cells

| DRUG TREATMENT (days 0, 4, 8; serum collected on day 9) | CHEMOTACTIC INDEX | |
|---|---|---|
| | Exp. 1 | Exp. 2 |
| G1: Control (no cyclosporine) | 1.76 | 1.60 |
| G2: CreL 0.15 ml of 25% dilution | 1.78 | 1.50 |
| G3: 5.0 mg/kg cyclosporine-CreL | 1.50 | 1.19 |
| G4: 15.0 mg/kg cyclosporine-CreL | 1.17 | 1.00 |
| G5: 5.0 mg/kg cyclosporine-MLVs | 1.07 | 1.00 |
| G6: 15.0 mg/kg cyclosporine-MLVs | 0.89 | 0.78 |

In the testing reported in Example 9, C57BL/6J mice were treated with 3 doses (days 0, 4 and 8) of either cyclosporine-CreL or cyclosporine-MLVs. Control mice G1 received no treatment and G2 were treated with CreL Mice were sacrificed on day 9 and T cells were isolated as the mixed lymphocyte band using Neutrophil Isolation Media (NIM) and pooled from 5 mice/group. Results are from 4 repetitions of 5 mice/group and reported as the mean chemotactic index.

In Experiment 1, non-cyclosporine treated mice showed an index of 1.76 whereas mice treated with either 5 or 15 mg/kg cyclosporine-CreL showed a 15% and 33% reduction in chemotactic index, respectively, compared to the untreated mice. The indices of mice treated with 5 or 15 mg/kg cyclosporine-MLVs were 39% and 49%, respectively, lower than the untreated mice. Replication of this experiment showed very similar results with a decrease in chemotactic activity of 26% and 37% for 5 and 15 mg/kg cyclosporine-CreL, respectively, and a reduction of 37% and 51% for 5 and 15 mg/kg cyclosporine-MLVs, respectively. In both experiments the immunosuppressive activity of 15 mg/kg cyclosporine-CreL and 5 mg/kg cyclosporine-MLVs were comparable. CreL alone showed no significant reduction in PHA-stimulated T-cell activity.

EXAMPLE 10

To determine if cyclosporine-MLVs and cyclosporine-CreL had comparable immunosuppressive B-cell activity on the primary and secondary response to sRBC challenge, C57BL/6J mice were treated three times with either form of the drug following either one or two antigenic challenges. The Jerne plaque assay and a hemagglutination assay were used to measure the B-cell response. To obtain additional information about the nature of the antibody produced in the response, both a direct and indirect Jerne plaque assay was performed on each sample to determine IgM and IgG titers, respectively. In the experiment designed to study the effect of cyclosporine on the primary response to sRBC, the mice were inoculated with sRBC on day 0, and treated with cyclosporine on days 0, 4 and 7. The Jerne plaque assay from sRBC challenged, control mice in this experiment showed 560 PFU $10^6$ cells from the direct assay (IgM response) and 1040 PFU from the indirect assay (combined IgM and IgG response). Mice treated with 5 mg/kg cyclosporine-CreL showed a slightly increased number of plaques in both the direct and indirect assays compared to the control mice. Mice treated with 5 mg/kg cyclosporine-MLVs, however, showed a 3.5-fold decrease in plaque number in the direct assay, when compared to the control mice. These data indicate that cyclosporine-MLVs are more immunosuppressive for IgM production in the primary response than cyclosporine-CreL at low doses.

When the hemagglutination titers from the above mice were examined, the data was similar in some respects to the plaque assays. The mice treated with 5 mg/kg of cyclosporine-CreL or cyclosporine-MLVs showed a 1.7-fold and 5-fold decrease in titer, respectively, compared to the sRBC challenged control mice.

When the secondary response of the sRBC challenged and cyclosporine treated mice were examined, mice were given sRBC on days 0 and 4, and cyclosporine (5 mg/kg) on days 4, 6 and 8. The IgM response of cyclosporine-CreL mice was similar to the control mice, but showed no change in plaque number in the indirect assay, suggesting a suppression of the IgG response to sRBC in these mice. Mice treated with cyclosporine-MLV, however, showed a decrease in both IgM and IgG response to sRBC compared to the control mice. These data again demonstrate the greater immunosuppressive activity of cyclosporine-MLV compared to equivalent doses of cyclosporine-CreL.

EXAMPLE 11

To study the effect of prophylactic treatment of mice with cyclosporine-MLVs or cyclosporine-CreL on the murine B-cell and T-cell response, mice were treated prophylactically with one dose of either cyclosporine-MLVs or cyclosporine-CreL, while control mice received no drug treatment, prior to sRBC challenge. From the Jerne plaque assay one can see that sRBC-challenged, control mice showed plaque levels of 560 PFU/$10^6$ cells, and mice treated with 15 mg/kg cyclosporine-CreL on either −1 or −2 days before antigen challenge, showed similar, but lower (420 and 520, respectively) plaque levels to those of the control mice. On the other hand, mice treated with 15 mg/kg cyclosporine-MLVs, on either −1 or −2 days prior to sRBC challenge, had 54% (300) and 50% (280), respectively, lower numbers of plaques in the assay compared to the control. The mice treated with 15 mg/kg cyclosporine-MLVs at −1 or −2 days showed a 28.6% and 46%, respectively, reduction in plaques compared to mice given equivalent doses of cyclosporine-CreL. Mice treated therapeutically with 3 doses of 5 mg/kg cyclosporine-MLVs (at days 0, 4 and 8) showed the best plaque reduction with a 3-fold decrease in number of plaques (180) compared to the control.

Results were also obtained from a hemagglutination assay done on the sera of mice in the above study, as seen in Table 7.

TABLE 7

Antibody Titer (sRBC Challenge) with One Dose

| DRUG TREATMENT (serum collected day 9) | TITER |
|---|---|
| G1: Control (sRBC only) | 1:1365 |
| G2: 15.0 mg/kg cyclosporine-CreL (day-1) | 1:682 |
| G3: 15.0 mg/kg cyclosporine-CreL (day-2) | 1:682 |
| G4: 15.0 mg/kg cyclosporine-MLVs (day-1) | 1:256 |
| G5: 15.0 mg/kg cyclosporine-MLVs (day-2) | 1:21 |
| G6: 5.0 mg/kg cyclosporine-MLVs (day 0, 4, 8) | 1:16 |

In the above experiment, C57BL/6J mice were inoculated with 0.2 ml of 10% sRBC IP on days 0 and 4. The mice were also treated with one intravenous dose (on either day −2 or −1 relative to sRBC challenge) of 15 mg/kg cyclosporine-CreL or cyclosporine-MLVs. Control mice G1 were inoculated with sRBC on days 0 and 4 but not treated with cyclosporine and G6 mice were inoculated with sRBC and treated therapeutically with 3 doses (days 0, 4 and 8) of 5 mg/kg cyclosporine-MLVs. All mice were sacrificed on day 9 and a hemagglutination assay was done on sera pooled from 5 mice/group. Results are from 3 repetitions of 5 mice/group reported as the mean titer.

Mice challenged with sRBC and given no cyclosporine treatment showed titers of 1:1365. Mice treated with 15 mg/kg cyclosporine-CreL on day −1 or −2 showed a 2-fold decrease in titer compared to the controls. There was a 32-fold greater decrease in the antibody titer of mice treated with 15 mg/kg cyclosporine-MLVs on day −2, compared to a comparable dose of cyclosporine-CreL. In addition, mice treated with 15 mg/kg cyclosporine-MLVs on day −2 had antibody titers comparable to those of mice treated therapeutically with 3 doses of 5 mg/kg cyclosporine-MLVs. This data demonstrates that a single dose of cyclosporine-MLVs, unlike a comparable dose of cyclosporine-CreL, can be used prophylactically to effectively suppress the immune response to sRBC.

When the T-cells from the above mice were treated with PHA and examined for chemotaxin production, the chemotactic indices of the cyclosporine-CreL and the cyclosporine-MLVs treated mice were not the same. Non-cyclosporine treated, control mice showed an average index of 1.46, and mice treated with 15 mg/kg cyclosporine-CreL on day −1 or −2 both had indices similar to that of the control mice. Mice treated with 15 mg/kg cyclosporine-MLVs on day −1 or −2, however, showed indices 26% and 32%, respectively, lower than that of the control mice. The mice treated with cyclosporine-MLVs on day −1 or −2 showed a 23% and 29%, respectively, lower index than mice treated with a comparable dose of cyclosporine-CreL. The mice treated with 15 mg/kg of cyclosporine-MLVs on day −2 demonstrated immunosuppression similar to that of mice treated therapeutically with 3 doses of 5 mg/kg cyclosporine-MLVs. This data suggests that both the T-cell response and the B-cell response can be effectively suppressed by prophylactic treatment with cyclosporine-MLVs, but not with equivalent doses of cyclosporine-CreL.

EXAMPLE 12

In this experiment, mice were challenged with lipopolysaccharide (LPS), a T-independent antigen, and treated with either cyclosporine-MLVs or cyclosporine-CreL to determine the effect of both agents on the murine B-cell response to this antigen. The control mice received only LPS. The results are shown in Table 8.

TABLE 8

Antibody Titer (LPS Challenge) of Mice Treated with Three Doses

| DRUG TREATMENT (days 0, 4 and 8; serum collected day 9) | TITER |
|---|---|
| G1: Control (No liposomes, No cyclosporine) | 0 |
| G2: Control (sRBC only) | 1:85 |
| G3: CreL 0.15 ml of 25% dilution | 1:85 |
| G4: Empty-Liposomes 0.15 ml (Comparable to 25 mg/kg cyclosporine-MLVs) | 1:85 |
| G5: 5.0 mg/kg cyclosporine-CreL | 1:85 |
| G6: 15.0 mg/kg cyclosporine-CreL | 1:85 |
| G7: 5.0 mg/kg cyclosporine-MLVs | 1:11 |
| G8: 15.0 mg/kg cyclosporine-MLVs | 1:13 |

In Example 12, the B-cell response of C57BL/6J mice inoculated with 1.0 mg of LPS, IV on days 0 and 4 was examined. The mice in G5, G6, G7, and G8 were also treated with 3 intravenous doses (days 0, 4 and 8) of cyclosporine-CreL or cyclosporine-MLVs. Control mice (G1) were treated with neither cyclosporine nor LPS, G2 were inoculated with LPS but not treated with cyclosporine, G3 were inoculated with LPS and treated with CreL and G4 were inoculated with LPS and treated with empty-liposomes. All mice were sacrificed on day 9 and a hemagglutination assay was done on sera pooled from 5 mice/group. Results are from 3 repetitions of 5 mice/group, reported as the mean titer.

When mouse sera was analyzed for antibody titers to LPS, non-cyclosporine treated, control mice showed an average titer of 1:85. Mice treated with either CreL or Empty-L also had titers of 1:85 indicating no effect of these substances on the B-cell response to LPS. Similarly, mice treated with 5 or 15 mg/kg cyclosporine-CreL also showed no decrease in antibody titer compared to the control mice. However, mice treated with 5 or 15 mg/kg of cyclosporine-MLVs demonstrated a 7.7-fold and 6.5-fold decrease in titer, respectively, compared with both the control mice and mice administered a comparable dose of cyclosporine-CreL. The data indicates that cyclosporine-MLVs, unlike equivalent doses of cyclosporine-CreL, can suppress the B-cell response to a T-independent antigen The results also suggest, therefore, that the target of immunosuppression for the cyclosporine-MLVs may be the antigen-presenting macrophage which could affect the B-cell response to both T-independent and T-dependent antigens.

A one-tailed sign test was performed to determine the probability of difference between the use of cyclosporine-MLVs versus a comparable dose of cyclosporine-CreL. When each of the three immunological assays were tested, it was found that there was a 95% probability that cyclosporine-MLVs were significantly more immunosuppressive than comparable doses of cyclosporine-CreL.

Although this specification has been disclosed and illustrated with reference to particular applications, the principles involved are susceptible to numerous other applications which will be apparent to those skilled in the art. The invention is, therefore, to be limited only as indicated by the scope of the appended claims.

What is claimed is:

1. Therapeutic liposomes comprising (i) a neutral lipid, (ii) a negatively charged lipid selected from the group consisting of dimyristoyl phosphatidylglycerol, dipalmitoyl phosphatidylglycerol, dilauryl phosphatidylglycerol, and dimyristoyl phosphatidic acid, and (iii) a cyclosporin, where the liposomes have a mean diameter of less than 200 nm and are stable on storage.

2. Liposomes of claim 1 wherein the negatively charged lipid consists of dimyristoylphosphatidylglycerol.

3. The liposomes of claim 1 wherein the neutral lipid comprises distearoylphosphatidylcholine.

4. The liposomes of claim 2 wherein the neutral lipid comprises distearoylphosphatidylcholine.

5. Therapeutic liposomes comprising (i) a neutral lipid, (ii) a negatively charged lipid selected from the group consisting of dimyristoyl phosphatidylglycerol, dipalmitoyl phosphatidylglycerol, dilauryl phosphatidylglycerol, and dimyristoyl phosphatidic acid, and (iii) cholesterol in amounts up to 50 mole percent of the neutral lipid, and (iv) a cyclosporin, where the liposomes have a mean diameter of less than 200 nm and are stable on storage.

6. Liposomes of claim 5 wherein the negatively charged lipid consists of dimyristoylphosphatidylglycerol.

7. The liposomes of claim 5 wherein the neutral lipid comprises distearoylphosphatidylcholine.

8. The liposomes of claim 6 wherein the neutral lipid comprises distearoylphosphatidylcholine.

* * * * *